United States Patent
Agassi et al.

(10) Patent No.: US 11,372,949 B1
(45) Date of Patent: Jun. 28, 2022

(54) DYNAMIC NARRATIVE VIEW GENERATION

(71) Applicant: CERNER INNOVATION, INC., Kansas City, KS (US)

(72) Inventors: Natalee Agassi, Blue Bell, PA (US); Emin Agassi, Blue Bell, PA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 790 days.

(21) Appl. No.: 15/803,385

(22) Filed: Nov. 3, 2017

Related U.S. Application Data

(60) Provisional application No. 62/417,908, filed on Nov. 4, 2016.

(51) Int. Cl.
*G06F 19/00* (2018.01)
*G16H 15/00* (2018.01)
*G16H 10/60* (2018.01)

(52) U.S. Cl.
CPC ........... *G06F 19/324* (2013.01); *G16H 10/60* (2018.01); *G16H 15/00* (2018.01)

(58) Field of Classification Search
CPC combination set(s) only.
See application file for complete search history.

(56) References Cited

U.S. PATENT DOCUMENTS

| | | | |
|---|---|---|---|
| 6,684,188 | B1 * | 1/2004 | Mitchell et al. |
| 10,504,198 | B1 * | 12/2019 | Ward |
| 2004/0172296 | A1 * | 9/2004 | Wohl |
| 2011/0264652 | A1 * | 10/2011 | Roberge et al. |
| 2012/0110016 | A1 * | 5/2012 | Phillips |
| 2012/0215560 | A1 * | 8/2012 | Ofek et al. |
| 2015/0095016 | A1 * | 4/2015 | Karres et al. |
| 2015/0379241 | A1 * | 12/2015 | Furst et al. |
| 2016/0048655 | A1 * | 2/2016 | Maitra et al. |

* cited by examiner

*Primary Examiner* — Michael Tomaszewski
*Assistant Examiner* — William T. Monticello
(74) *Attorney, Agent, or Firm* — Shook Hardy & Bacon LLP

(57) ABSTRACT

A concept type agnostic method, system and media is provided to dynamically generate a narrative view based on the template hierarchy levels, high-level attributes of the nodes in the document template hierarchy, and end user entry is provided.

18 Claims, 14 Drawing Sheets

CONCEPTUAL RELATIONSHIPS DIAGRAM 1:

```
              ┌──────────┐
              │   RISK   │
              │ FACTORS  │
              └──────────┘
               ↙        ↘
        ┌────────┐   ┌─────────────┐
        │ ASTHMA │   │ DEHYDRATION │
        └────────┘   └─────────────┘
```

PROVIDER DOCUMENTATION NARRATIVE:

RISK FACTORS ASTHMA, DEHYDRATION.

KDI CONFIGURATION:

| | PARAMETER (ENCODED) |
|---|---|
| ☐ RISK FACTORS | |
| ○ NONE | VALUE |
| ○ ASTHMA | VALUE |
| ○ OGRANIC OBS... | VALUE |
| ○ PULMONARY... | VALUE |
| ○ DEHYDRATION | PROBLEM |
| ○ ALERGIC REAC... | VALUE |

THE FOLLOWING ARE SELECTED IN THE PROVIDER DOCUMENTATION:

RISK FACTORS
ASTHMA
DEHYDRATION

*FIG. 3.*

| DOCUMENT TEMPLATE GENERAL MEDICAL (ADULT, FEMALE, PROVIDER, ED) | | |
|---|---|---|
| CONCEPT NAME | | CONCEPT ID |
| GENERAL MEDICAL (ADULT, FEMALE, PROVIDER, ED) | | 7440358 |

| | STRUCTURE ▼ | |
|---|---|---|
| CONCEPT DETAILS | + ✗ ✗ | |
| STRUCT... | | |
| ATTRIBUTES | NODE DISPLAY NAME | TYPE |
| CONTEXT | ⊞ ARRIVAL INFORMATION | DOCUMENT SELECTION |
| NAMES | ⊟ HPI | DOCUMENT SELECTION |
| REFERENCES | ⊟ HPI GENERAL MEDICAL | OBSERVATION QUESTION TREE |
| INTERFACES | ⊟ ■ PRIMARY COMPLAINT | OBSERVATION QUESTION (ENC... |
| TEXT/LINKS | ⊟ GENERAL MEDICAL | PROBLEM |
| STATUS | ⊞ ■ GENERAL MEDICAL DETAILS | PARAMETER SET |
| REVIEW/APPROVAL | ■ COMPLAINT SPECIFIED | PARAMETER (TEXT) |
| | ⊞ ■ TIMING | PARAMETER SET |
| | ⊞ ■ OCCURRED AT | PARAMETER (ENCODED) |
| | ⊞ ■ PAIN | PARAMETER (ENCODED) |
| | ⊞ ■ ASSOCIATED SYMPTOMS | PARAMETER (ENCODED) |
| | ⊞ ■ RISK FACTORS | PARAMETER (ENCODED) |
| | ⊞ ■ SIMILAR SYMPTOMS/EVENT | PARAMETER (ENCODED) |
| | ⊞ OTHER | VALUE |
| | ■ PRIMARY COMPLAINT DETAILS | OBSERVATION QUESTION (TEXT) |
| | ⊞ HPI SECONDARY COMPLAINT | OBSERVATION QUESTION TREE |
| | ⊞ ALLERGIES | DOCUMENT SELECTION |

*FIG. 5.*

| DOCUMENT TEMPLATE GENERAL MEDICAL (ADULT, FEMALE, PROVIDER, ED) | | |
|---|---|---|
| CONCEPT NAME | | CENCEPT ID |
| GENERAL MEDICAL (ADULT, FEMALE, PROVIDER, ED) | | 7440358 |

| CONCEPT DETAILS STRUCT.... | ⊗ STRUCTURE ▼ + ✗ ✗ ◢ | |
|---|---|---|
| ATTRIBUTES | NODE DISPLAY NAME | TYPE |
| CONTEXT | ⊟ ■ PRIMARY COMPLAINT | OBSERVATION QUESTION (ENC... |
| NAMES | ⊟ ⊗ GENERAL MEDICAL | PROBLEM |
| REFERENCES | ⊞ ■ GENERAL MEDICAL DETAILS | PARAMETER SET |
| INTERFACES | ■ COMPLAINT SPECIFIED | PARAMETER (TEXT) |
| TEXT/LINKS | ⊞ ■ TIMING | PARAMETER SET |
| STATUS | ⊞ ■ OCCURRED AT | PARAMETER (ENCODED) |
| REVIEW/APPROVAL | ⊞ ■ PAIN | PARAMETER (ENCODED) |
| | ⊞ ■ ASSOCIATED SYMPTOMS | PARAMETER (ENCODED) |
| | ⊞ ■ RISK FACTORS | PARAMETER (ENCODED) |
| | ⊞ ■ SIMILAR SYMPTOMS/EVENT | PARAMETER (ENCODED) |
| | ⊞ ▦ OTHER | VALUE |
| | ■ PRIMARY COMPLAINT DETAILS | OBSERVATION QUESTION (TEXT) |
| | ⊞ ■ HPI SECONDARY COMPLAINT | OBSERVATION QUESTION TREE |
| | ▭ ALLERGIES | DOCUMENT SELECTION |
| | ▭ MEDICATIONS | DOCUMENT SELECTION |
| | ▭ HISTORY | DOCUMENT SELECTION |
| | ▭ ROS | DOCUMENT SELECTION |
| | ▭ EXAM | DOCUMENT SELECTION |

*FIG. 6.*

| CONCEPT NAME | | CONCEPT ID | |
|---|---|---|---|
| ABDOMINAL PAIN (ADULT, FEMALE, PROVIDER, ED) | | 1504062 | |
| CONCEPT DETAILS | ⊛ STRUCTURE ▶ | | |
| STRUCT... | ◆ × × | | |
| ATTRIBUTES | NODE DISPLAY NAME | TYPE | |
| CONTEXT | ⊞ ■ EYELIDS | OBSERVATION QU... | |
| NAMES | ⊞ ■ CONJUNCTIVE | OBSERVATION QU... | |
| REFERENCES | ■ SCLIRE | OBSERVATION QU... | |
| INTERFACES | ⊟ ■ RETINAL EXAM | OBSERVATION QU... | |
| TEXT/LINKS | ⊟ ■ LEFT EYE | OBSERVATION QU... | |
| STATUS | ⊞ ■ SLIT LAMP / OPHTHA... | OBSERVATION QU... | |
| REFERAL/ | ⊞ ■ IOP | OBSERVATION QU... | |
| APPROVAL | ⊟ ■ OPTIC DISC | OBSERVATION QU... | |
| | ■ SHARP DISC MARG... | VALUE | |
| | ⊛ PAPILLEDEMS | PROBLEM | |
| | ■ MARGINS IRREGUL... | VALUE | |
| | ■ COLOR IRREGULAR | VALUE | |
| | ⊟ ■ OPTIC CUP | VALUE | |
| | ⊟ ■ OPTIC CUP DET... | PARAMETER SET | |
| | ⊟ ■ FORMATION | PARAMETER (ENC... | |
| | ■ NORMAL | VALUE | |
| | ■ ABSENT | VALUE | |
| | ■ ENLARGED | VALUE | |
| | ■ DEEP | VALUE | |
| | ■ OTHER | VALUE | |
| | ■ COMMENTS | PARAMETER (TEXT) | |
| | ■ OTHER | VALUE | |

*FIG. 7.*

Arrival Information
Documentation Reviewed: EMS Records
Provider Type: Attending i Time Seen: 9/19/2014, 10:55 AM
Historian: ParentHPI
History Limited by: Mental Status Altered
Chief Complaint
    HPI General Medical Details TEST: Duration: 3 Days; Timing: Gradual; Location: Pain all over and back;
Exacerbated by: Nothing; Relieved by: Nothing; Quality: Sharp; Severity: Severe {7-1 0}; Similar Event Yes
       Associated Symptoms: Nausea and Fatigue -- No Fever
Complaint Details: PT has pain in legs and back for the last 3 days. He also c/o urethral discharge.
History
Allergies and Medications TEST:
    Allergies:
        Not Assessed Medications:
No data available a1 this time.

Medical History: other: Hemoglobin SS Disease w/ Crisis
Social History:
    Smoker: No
    Illicit Drug User Yes;
Comment: Cocaine
Family History:
    Member: Mother
        Mother Details:
            Problems: Diabetes
            Additional Detail: Sickle Cell Anemia ROS
 Comprehensive ROS Details TEST:
    Constitutional: Fatigue -- No Fever
    Eye: Denies Symptoms
    Ear/ Nose/ Throat: Denies Symptoms
    Cardiovascular: Denies Symptoms
    Respiratory: Denies Symptoms
    Genitourinary: Urethral Discharge
    Neurological: Denies Symptoms
    Musculoskeletal: Back Pain
    Skin: Denies Symptoms
    Hematologic I Lymphatic: Fatigue
Exam
Vitals Details TEST:
    I have reviewed Hie vital signs documented in this visit: Yes/ Time: 9/19/2014, 11 :01 AM
No data available at this time.
Constitutional:
Constitutional (Target Exam) TEST: CONSTITUTIONAL: No Acute Distress; Alert and Moderate
Distress
Eyes:
EYES: EYES: ic1eric
Ear/ Nose / Throat:
    ENT (Target Exam) TEST: ENT: Oropharynx Clear and EXPANDED DETAILS
    Ear Nose Throat (Detailed Exam) TEST: Nose Inspection: Tenderness

Cardiovascular:
    Cardiovascular (Target Exam) TEST: CARDIAC: RRR; No Murmurs and No Extremity Edema Respiratory:
    Respiratory (Target Exam) TEST: RESPIRATORY: Clear to Auscultation BIL
Abdomen I Rectum:
    Abdomen Rectum (Target Exam) TEST: ABDOMEN/ RECTUM: Soft; NT; +BS and Non Distended
Musculoskeletal:
    Musculoskeletal (Target Exam) TEST: Comment: Bilateral Knees, No erythema or crepitus noted on
Exam
Neurological:
    Neurological (Target Exam) TEST: NEURO: AAOx3: No Acute Distress and Nonfocal
Skin:
    Skin (Target Exam} TEST: SKIN: Warm; Dry and No Rash
Psychological:
    Psychological (Target Exam) TEST: MENTAL STATUS: Appropriate Affect
Lymphatic:
    Lymphatic (Target Exam) TEST: LYMPH: Lymphadenopathy and Anterior Cervical LAD
Genitourinary:
    Genitourianry (Target Exam) TEST: Genitourinary Condensed Examination: Male Exam
    Male Genitouririary (Detailed Exam) Test: Male GU Exam: No Circumcision and Not Testicular
Enlargement Data Reviewed Old Records:
    Decision to Obtain Old Records (1 pt): Yes I Records Reviewed: Prior Medical Records
    Summary of Old Records (2 pts): He was in last week for same.
Labs Ordered/Reviewed for this Visit (1 pt): Yes/ Interpretation (2 pts): HCT was 7.8 which is his base line of 8 from last week.
Laboratory Result Discussion with Patient and or Family (CQM): Yes Labs/ EKG/ Radiology Labs:
No data available at this time.

ECG: The document template has a configuration error that is preventing the system from retrieving the patient data. Please contact your system administrator to have it corrected. You may use a different template for your documentation.
Radiology:
No data available at this time.

Consults

Consultations:
    Call Time: 9i19/2014, 11: 10 AM
    Provider Name/Group: SMITH, RANDALL N - NonStaff Physician Diagnosis Medical Decision Making:
i have considered AMI, Septic Arthritis, Lupus Arthritis, Gout.
PT. is nontoxic appearing and tolerating PO fluid in the ED.
He has Plans to follow up with Dr. Smith this week he was told to return if worsening symptoms, Fever, Shortness of Breath or any concerns Diagnosis Detail: Differential Diagnosis: Acute MI, Acute Upper Respiratory Infection, Gastroenteritis and Pneumonia
other: Urethritis and Hemoglobin SS Disease w/ Crisis Disposition Disposition: Discharge
    Discharge Details
        Decision Time: 9/19/2014, 11:16AM
        Discharged to: Home
        Emergency Room Management Options: Management Options: New problem with additional work up plan (4 pts)
        Patient Condition: Stable
        Comment: Pt plans to follow up with Dr. Smith to have recheck and schedule ortho eval of joint pain.

Electronically signed by ad min admin, PA on 09/19/2014 11: 17 AM

*FIG. 8.*
CONTINUED

Arrival Information

| | |
|---|---|
| Documentation Reviewed | EMS Records. |
| Provider Type | Attending Time Seen 09/19/2014 9:40. |
| Historian | Parent. |

Arrival Information

| | |
|---|---|
| History Limited by | Mental Status Altered. |
| Chief Complaint | Pain all over<br>Duration 3 days, timing Gradual, Location pain all over and back Exacerbated by Nothing, Relieved by Nothing, Quality Sharp, Severity Severe (7-10), Associated symptoms Nausea, Fatigue, No Fever; Prior Similar Event |
| Complaint Details | Pt. has pain in legs and back for the last 3 days. He also c/o urethral discharge. |

History

| | |
|---|---|
| Allergies and Medications | Not Assessed. |
| Medical History | Hemoglobin SS Disease w/ Crisis |
| Social History | Non Smoker, Illicit Drug User Cocaine. |
| Family History | Mother Problems: Diabetes, Sickle Cell Anemia |

ROS

| | |
|---|---|
| Comprehensive ROS | Constitutional Fatigue, No Fever.<br>Eye Denies Symptoms.<br>Ear / Nose / Throat Denies Symptoms,<br>Cardiovascular Denies Symptoms.<br>Respiratory Denies Symptoms.<br>Genitourinary Urethral Discharge.<br>Neurological Denies Symptoms.<br>Musculoskeletal Back Pain<br>Skin Denies Symptoms<br>Hematologic / Lymphatic Fatigue |

Exam

| | |
|---|---|
| Vitals | Reviewed on 9/19/2014 11:01 AM |
| Constitutional | No Acute Distress, Alert, Moderate Distress. |
| Eyes | |

| External Structures | Left Eye | Right Eye |
|---|---|---|
| Sclera | Icteric | Icteric |

Slit Lamp

| Retinal Exam | Left Eye | Right Eye |
|---|---|---|
| IOP | 12mmHg | 14mmHg |
| Optic Disk | Sharp disk margins | Sharp disk margins |
| Optic Disk Ratio | 0.4 | 0.4 |

| | |
|---|---|
| Ear / Nose / Throat | Oropharynx Clear, Dry Membranes; Nose Inspection Tenderness. |
| Cardiovascular | RRR, No Murmurs, No Extremity Edema. |
| Respiratory | Clear to Auscultation B/L. |
| Abdomen / Rectum | Soft, NT, +bs and Non Distended |
| Musculoskeletal | Swelling; Bilateral Knees, No erythema or crepitus noted on Exam. |
| Neurological | AAOx3, No Acute Distress, Nonfocal. |
| Skin | Warm, Dry, No Rash. |
| Psychological | Appropriate Affect. |
| Lymphatic | Lymphadenopathy, Anterior Cervical LAD. |
| Genitourinary | No Circumcision, No Testicular Enlargement. |

| | | |
|---|---|---|
| Reviewed | | |
| | Old Records | Summary of Old Records (2pt) He was in last week for same. Interpretation (2pt) HCT was 7.8 which is his base line of 8 from last week. Laboratory Result Discussion with Patient and or Family (CQM).<br>Labs Ordered/Reviewed for this Visit. |
| Consults | | |
| | Consultations | 9/19/2014 11:10 AM, Provider Name/Group SMITH, RANDALL N NonStaff Physician. |
| Diagnosis | | |
| | Medical Decision Making | I have considered AMI, Septic Arthritis, Lupus Arthritis, Gout. PT. Is nontoxic appearing and tolerating PO fluid in the ID. He has Plans to follow up with Dr. Smith this week he was told to return if worsening symptoms, Fever, Shortness of Breath or any concerns. |
| | Differential Diagnosis Detail | Acute MI, Acute Upper respiratory Infection, Gastroenteritis, Pneumonia, Urethritis, Hemoglobin SS Disease w/ Crisis. |
| Disposition | | |
| | Disposition | Discharge to Home: 9/19/2014 11:16 AM. Patient Condition Stable. Management Options: New problem with additional work up plan Comment: Pt plans to follow up with Dr. Smith to have recheck and schedule ortho eval of joint. |

*FIG. 9.*
CONTINUED

| HPI | |
|---|---|
| Primary Complaint | Asthma/Wheeze Onset Prior to Arrival 5 Hours, Onset Rate Gradual, Timing Pattern Continuous, Progression Deteriorated; Occurred at Home, Pain No. Associated Systems Dyspnea, Chest Discomfort Comment Tachypnea; Risk Factors Resolved PNA 2 weeks ago. |
| Primary Complaint Details | Prolong expiration and use of accessory muscles. |

FIG. 10A

| HPI | |
|---|---|
| Primary Complaint | Asthma/Wheeze Onset Prior to Arrival 5 Hours, Onset Rate Gradual, Timing Pattern Continuous, Progression Deteriorated; Occurred at Home, Pain No. Associated Systems Dyspnea, Chest Discomfort Comment Tachypnea; Risk Factors Resolved PNA 2 weeks ago. |
| Primary Complaint Details | Prolong expiration and use of accessory muscles. |

FIG. 10B

DYNAMIC NARRATIVE VIEW GENERATION

This application claims the benefit of U.S. Provisional Application No. 62/417,908, entitled "Dynamic Narrative View Generation," filed Nov. 4, 2016, which is expressly incorporated by reference in its entirety.

BACKGROUND

Narrative medicine is practiced by numerous doctors and takes into account individuals' narratives in the treatment process. Typically, narrative medicine accesses an individual's story including relational and psychological conditions in addition to physical symptoms and test results included in the individual's medical chart.

Doctors and treatment providers using a narrative view may be able to provide an individual centered care plan that may provide additional clues into the individual's health and encourages a holistic view to individual medical care management. Those using the narrative medicine approach often prefer to view a vertical narrative of the individual's seeking medical care's story and may wish to customize the narrative view according to the care provider's treatment practice.

However, current object-oriented computer programming used for medical documentation assigns concept or class types to objects documented electronically in the medical process. When medical documentation objects are assigned a concept types in object-oriented computer programming, the computer generated narrative output of this information is hard to predict and may sometimes be missing key pieces of medical documentation for the narrative. In addition, custom narrative templates are unable to be generated when medical documentation objects are assigned a concept type due to the large number of concept types, combinations of concept types and syntax rules.

SUMMARY

Embodiments of the present invention provide an organized and readable medical narrative output or graphical indicia for use by a doctor or treatment professional for medical treatment of an individual.

The claimed invention relates to a system and method supporting computerized healthcare information systems. More specifically, the claimed invention relates to a system, method and computer readable media for creating nested relationships between high level objects and child objects in a documentation template hierarchy for generating a dynamic concept type agnostic medical narrative.

The claimed solution is necessarily rooted in computerized electronic medical documentation technology in order to overcome a problem specifically arising in the realm of computer medical information documentation. The claims address the problem of documenting computer medical information for structured and non-structured medical information documentation in concept type agnostic form such that a narrative view is generated based on template hierarchy levels, high level attributes of the nodes in the documentation template and end user entry.

If adhering to the routine, conventional medical documentation and generation of a medical narrative view of documented computer medical information, medical object data documentation is content type specific and only applicable to structured content. In conventional medical information documentation, syntax, concatenation and style rules are dependent on specific concept types and their structural composition (e.g., question and values combination, encoded parameter and values combination and text and numeric questions). New syntax, concatenation and style rules must be developed whenever new concept types and/or their combinations are introduced. As such, medical information documentation content builders are not able to follow and test all of the rules and their instances due to the large number of concept types, their combinations and syntax rules. In addition, there are no default or custom narrative configurations using routine conventional concept type documentation and it is hard to predict the output when the content builder is building or configuring different computer medical information documentation templates.

The claimed invention overcomes the limitations of current computer medical information documentation by using concept type agnostic methods and systems to generate narrative medical views.

The claimed system and method of the present application represents a new paradigm in object based computer medical documentation. Not only does the claimed invention generate and provide an organized and readable medical narrative for an individual based on concept type agnostic medical documentation, but makes the individual's care more efficient and cost-effective.

Content builders utilizing object based concept agnostic medical documentation according to the claimed invention will notice improved ability to build custom and configurable narrative layouts for doctors and medical providers and reduces the overall time to setup a narrative view for a doctor of medical provider. In addition, the method and system for concept type agnostic medical documentation reduces possible safety issues by making the system easier to test and maintain by removing the concept types and having to reconfigure each time a new concept type is added. This can reduce the number of "clicks" or entries a computer user has to make to build and generate a dynamic medical narrative view thereby in reducing the memory utilization, CPU cycles, number of operations that need to be performed by the computer, and power consumption. The resulting cost savings and operational efficiencies of a computer electronic medical record magnify the potential benefits of this technology.

BRIEF DESCRIPTION OF THE DRAWINGS

Embodiments are described in detail below with reference to the attached drawing figures, wherein:

FIGS. 3-4 are flow diagrams depicting concept type agnostic medical documentation utilizing nesting levels in a document template hierarchy to generate a medical narrative output;

FIGS. 5 and 6 depict flow diagrams of concept type dependent medical type documentation;

FIG. 7 is a flow diagram depicting concept type agnostic medical documentation;

FIG. 8 depicts a medical narrative output or graphical indicia from concept type dependent medical documentation;

FIG. 9 depicts a medical narrative output or graphical indicia from concept type agnostic medical documentation;

FIG. 10A depicts a graphical indicia of concept type agnostic rules and document template hierarchy view layout; and FIG. 10B depicts a graphical indicia of a generated medical narrative.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for a system and method for creating a nested relationship between a high level object and a child object in a documentation template hierarchy for generating a dynamic medical narrative.

Figure 1:
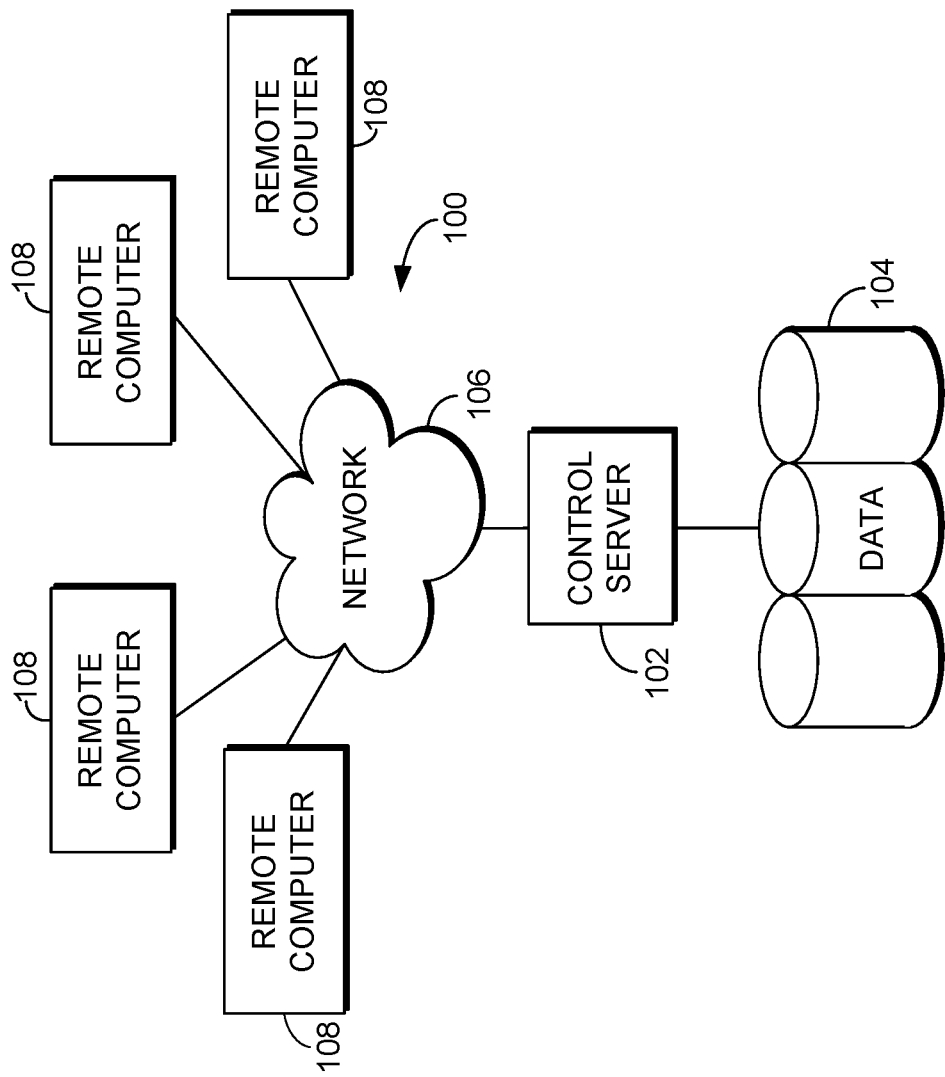
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
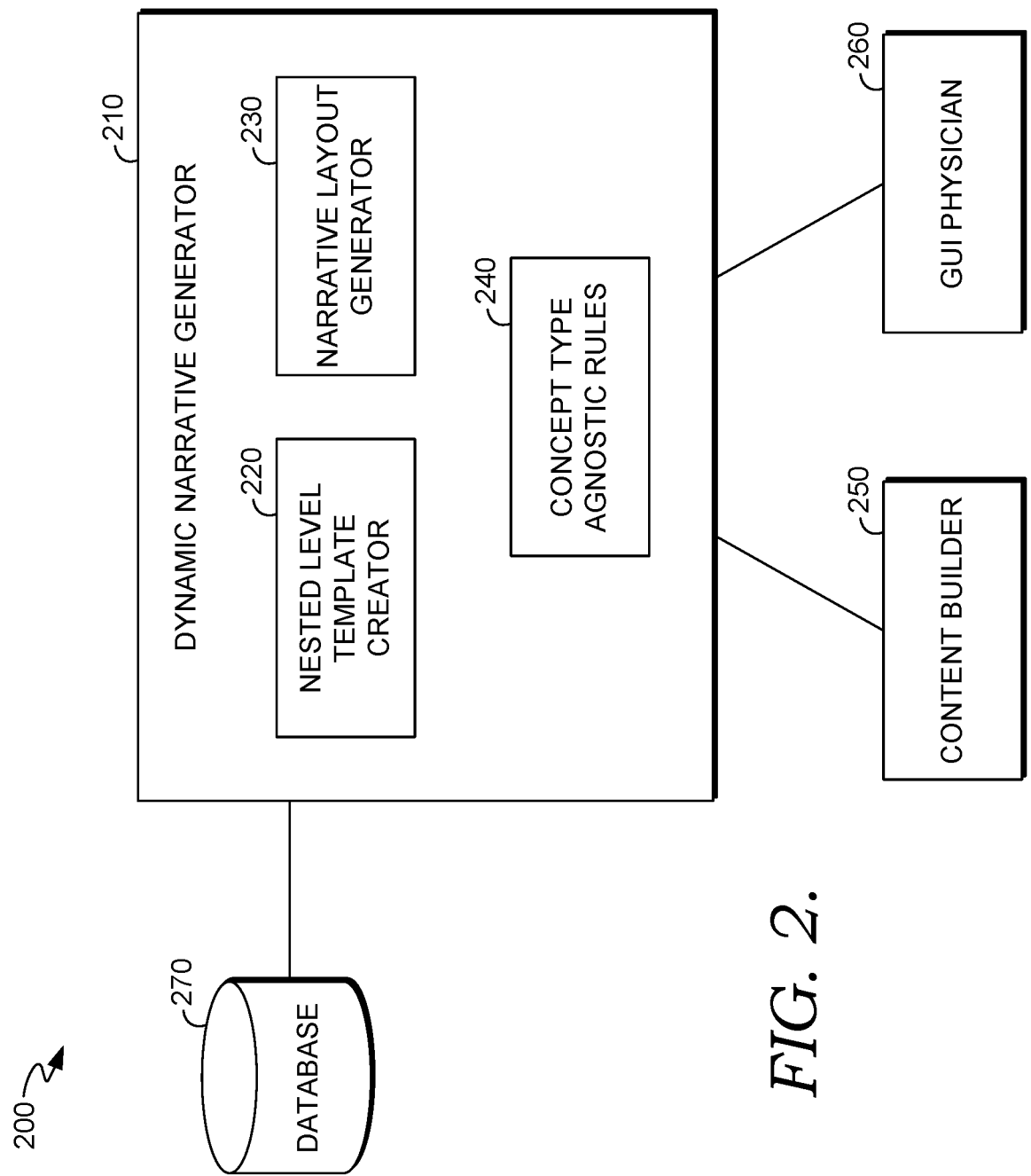
FIG. 2 is an exemplary system architecture suitable to implement embodiments of the present invention.

In an embodiment 200 exhibited by FIG. 2, the processing duties may be split among several computing systems. The data store 270 may be implemented through a database system and may be an electronic medical record or electronic health record. The network (not shown), such as the internet or other public or private network, serves as a communications link to content builder devices 250 and provider devices and graphical interface displays 260. The tasks performed by the processor utilize a variety of computer technology. In one embodiment, the technology can be divided into three tiers, web server, application server and database server. Each tier is comprised of a number of system layers as described below.

Dynamic Narrative Generator 210 is comprised of sub-components including nested level template creator 220, narrative layout generator 230 and concept type agnostic rules catalog 240. Dynamic Narrative Generator 210 is also in communication content builder device 250, care provider device 260 and data store 270. Data store 270 may be a database with patient records, such as an electronic medical record.

Nested Level Template Creator 220 is in communication with content builder device 250.

Figure 4:
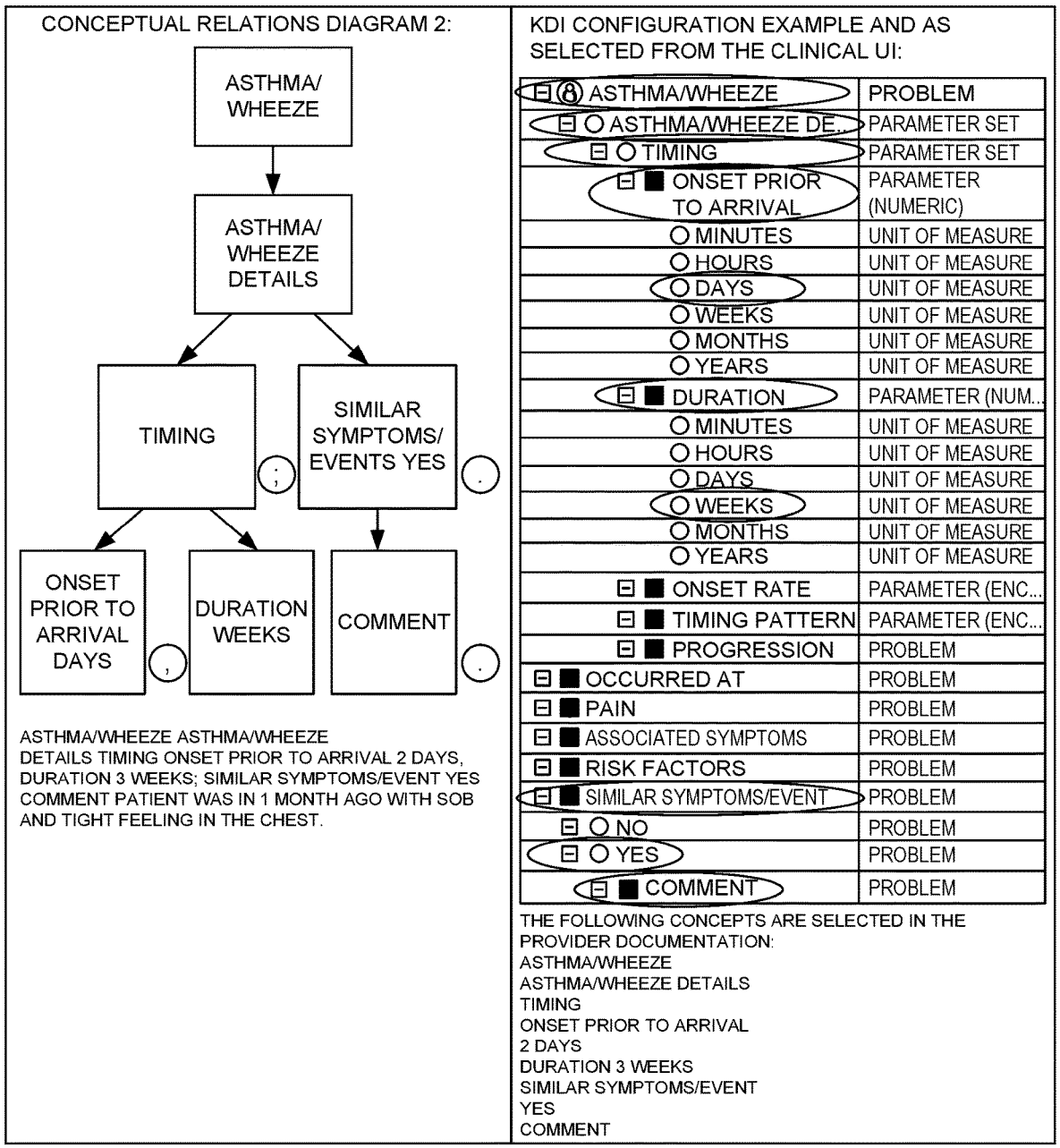

Concept Type Agnostic Rules Catalog provides default rules based on nested levels created using the Nested Level Template Creator 220. Default rules produce predictable, readable and structured output. The Concept Type Agnostic Rules Catalog 240 maintains the rules to be applied to the nested levels created by a content builder 250 using nested level template creator 220. The rules use the following configurable sample concatenation and punctuation. For example, nested level 1 is a Section Header in the document. Nested Level 2 contains all elements under the Question Tree (this level always starts from the new line underneath of nested level 1). Each subsequent nested level is concatenated to the parent level with a space. Each nested sibling level is separated from the subsequent sibling nested level by a comma. A semicolon (;) will be inserted between a parent and child of the subsequent parent. Each nested level 2 hierarchy will be concluded with a period. All nested elements under Nested Level 2 are concatenated and wrapped. Carriage returns in free text fields are not suppressed in the output narrative. The nested levels are shown in FIGS. 3, 4 and 7 and are discussed in more detail below.

Narrative Layout Generator 230 utilizes the Concept Type Agnostic Rules Catalog 240 to generate narrative content (text or non-text) concatenating using the rules based on nesting levels.

This also simplifies development by eliminating the need of adding new rules to support new concept types. This approach simplifies testing processes because it reduces special use cases based on new object concept types. The approach reduces total time required to setup narrative view, allows to easy customization of a narrative view and reduces possible patient safety issues.

Prior medical documents required a concept type for medical documentation objects did not provide a narrative view to a care provider. These system and methods were only applicable to structured content. Syntax, concatenation and style rules are dependent on specific concept types and their structural composition. These include, for example, question and values combination, encoded parameter and values combination, and text and numeric questions.

In prior methods and systems, if a narrative view were to be generated, new syntax, concatenation and style rules would have needed to be developed whenever new concepts and/or their combinations were introduced. This was too costly to justify providing a narrative view. Content builders were not able to follow and test all of the rules and their instances due to large number of types, their combinations, and syntax rules. There were no default and custom narrative configurations, thus, the output was hard to predict when building (configuring) document templates.

Oftentimes, doctors or treatment professionals prefer a medical narrative view arranged vertically. Depending on the practice type, treatment professionals may prefer the individual's medical narrative view to include arrival information, patient complaints, patient history, and review of symptoms, examination, data reviewed, consults, diagnosis and disposition.

A concept type agnostic method to dynamically generates narrative view based on the template hierarchy levels, high-level attributes of the nodes in the document template hierarchy, and end user entry are provided.

In the present application, content builders are not constricted to use specific concept types at each level. Content builders with knowledge of levels can modify content and still get predictable results. This approach should simplify testing process because it reduces special use cases. This also simplifies development by eliminating the need of adding new algorithms to support new concept types. Default rules produce predictable, mostly readable and structured output. This reduces total time required to setup narrative view and allows an easily customize default output. This also reduces possible patient safety issues and allows for configurable layout template at each node in the nested template hierarchy. Each template can include HTML formatting and syntax replacement pattern.

Narrative Layout Generator 230 generates the narrative view according to the specified concept type agnostic rules and customization that may be done by the content builder 250. For example, Native Layout Generator 230 can generate a text block view with unstructured text and/or provider notes but also configure tables, graph views, bulleted and/or numbered list layouts as the medical documentation objects are not tied to a concept type.

The Narrative Layout Generator 230 utilizes both the document template hierarchy of the Nested Level Template Creator 220 and concept type agnostic rules 240 to generate a narrative layout. The nesting levels in the document template hierarchy of the Nested Level Template Creator 220 directly affect narrative output of the Narrative Layout Generator 230. Each level in the document template hierarchy can contain set (question or parameter sets) and non-set concept types (section or question) and the levels can be nested. Each document template hierarchy can contain multiple nested levels. The Concept Type Agnostic Rules Catalog applies punctuation rules based on the nesting levels. The narrative content (text or non-text) is concatenated using the concept type agnostic rules based on nesting levels. For example, the application uses the configurable sample concatenation and punctuation rules below.

For example, the two column medical narrative graphical indicia shown generated and shown in FIG. 10A is based on the concept type agnostic rules and the document template hierarchy view layout. For example, the left column contains template section names and nested level 2 labels under the Question Tree as shown in FIG. 10A.

As shown in FIG. 10B in the generated medical narrative graphical indicia below, the right column contains charted or documented concept value objects under the Question Tree and all nested elements with their labels and values.

As can be seen in the example below and described in more detail below, the medical narrative is generated based on the concept level positions in the document template hierarchy. The high-level concept can contain a set and is concept type agnostic. The document template hierarchy provides predictable and consistent narrative output that is easy to read with minimal punctuation, easy to follow, test and maintain.

FIGS. 3-4 are flow diagrams depicting concept type agnostic medical documentation utilizing nesting levels in a template hierarchy for generating the medical narrative output. As can be seen in the right column FIG. 3, "Risk Factors" is a high level or level 1 concept in a document template hierarchy. Level 1 is a Section Header in the narrative document. Nested beneath "Risk Factors", Nested Level 2 contains all elements under the Question Tree nested level 1: None, Asthma, Chronic Obstructive Pulmonary Disease, Pulmonary Embolism, Dehydration and Allergic Reaction. During object oriented medical documentation, the care provider selects "asthma" and "dehydration" as "risk factors" from the document template hierarchy. When a narrative layout is generated based on the document template hierarchy shown in FIG. 3 and concept type agnostic rules are applied, a readable narrative of "Risk Factors Asthma, Dehydration." is displayed as a narrative graphical indicia.

As can be seen in the right column of FIG. 4, "Asthma/Wheeze" is a Problem and is a high level or level 1 concept in a document template hierarchy. Again, Level 1 is a Section header in the narrative document. Nested beneath "Asthma/Wheeze" are nested level 2 concepts of "timing", "occurred at", "pain", "associated symptoms", "risk factors" and "similar symptoms/event". Nested beneath level 2 concept "timing" are level 3 concepts "onset prior to arrive" and "duration".

Nested beneath level 3 concept "onset prior to arrival" are level 4 concepts "minutes", "hours", "days", "weeks", "months" and "years". Nested beneath level 2 concept "similar symptoms/event" are nested level 3 answer concepts "no" and "yes". Beneath level 3 concept "yes" is a free text box for the care provider to enter free unstructured text information regarding the answer and the individual. During medical documentation, the care provider selects "asthma/wheeze" as a problem, along with "asthma/wheeze details". The care provider selects "timing" level 2 concept, level 3 concepts "onset prior to arrival" and "duration" under "timing level 2 concept. The care provider then selects" "days" for level 4 concept under "onset prior to arrival" level 3 concept and "weeks" for level 4 concept under "duration" level three concept. The care provider also selects level 2 concept "similar symptoms/event" and level 3 concept "yes" beneath "similar symptoms" concept level 2. The care provider inputs the following into the free text nested under level 3 concept "yes": "Patient was in 1 month ago with SOB and tight feeling in the chest."

When a narrative layout is generated based on the document template hierarchy shown in FIG. 4 and concept type agnostic rules are applied, a readable narrative of the concepts selected by the care provider and the free text input is displayed as a readable narrative graphical indicia as shown in the lower left column of FIG. 4. This is unlike concept type constrained documentation which is limited to structured text.

FIGS. 5 and 6 depict a flow diagram depicting concept type dependent medical type documentation. As can be seen in FIGS. 5 and 6, the concepts that are tied to concept type do not have the logical nesting that is provided by a concept agnostic document template hierarchy and rules as described above. As can be seen in FIGS. 5 and 6 the concepts are not logically nested as shown in FIGS. 4 and 5. For example, when the concepts are tied to concept type and are not logically nest "complaint specified" and "timing" are on the same level and "timing" is not nested beneath "complaint specified" in order to provide a proper narrative view.

FIG. 8 depicts a medical narrative output or graphical indicia from concept type dependent medical documentation as shown in FIGS. 5 and 6. As can be seen in FIG. 8, the narrative view is several pages long, not easy to follow, poorly formatted, does not have the proper headers for a medical narrative view and is even missing documented information regarding the eye test.

FIG. 7, like FIGS. 3 and 4, includes logically nested concepts that provide a concise, easy to follow, well-formatted narrative view with proper headers and includes all the necessary documentation as can be seen in FIG. 9. FIG. 9 even provides a customized view of the Eye Exam in a table or graphical form that is easy for the care provider to quickly view in narrative form. In addition, document divisions, headers, change in font type, color, spacing and format can be customized when concepts are logically nested according to the claimed invention without and are not limited to a concept type.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more computer storage media having computer-usable instructions that, when used by one or more computing devices, cause the one or more computing devices to perform a method for creating nested relationship between a high level object and a child object in a documentation template hierarchy for generating a dynamic narrative view, the method comprising:
   receiving a first object of medical documentation for an individual via a medical narrative view documentation template hierarchy;
   receiving a second object of medical documentation for an individual via the medical narrative view documentation hierarchy;
   storing said first object of medical documentation as a high level object in the medical narrative view documentation template hierarchy;
   storing said second object of medical documentation as a nested child object of the high level object in the medical narrative view documentation template hierarchy;
   storing the nested relationship between the high level object and the nested child object in the medical narrative view documentation template hierarchy;
   leveraging concept type agnostic rules for generating a medical narrative view for the patient to provide to a care provider;
   determining by a processor the medical narrative view for the patient by applying the concept type agnostic rules to the nested relationship in the documentation template hierarchy, wherein the concept type agnostic rules include configurable concatenation or punctuation for a plurality of nested levels; and
   providing a graphical user interface of the medical narrative view for the patient to a care provider, wherein medical narrative view is arranged vertically and comprises narrative headings and sections for multiple of patient arrival information, patient complaints, patient history, review of patient symptoms, patient examination, patient data reviewed, patient consults, patient diagnosis and patient disposition.

2. The media of claim 1, wherein the nested child object comprises multiple nested child objects.

3. The media of claim 2, wherein the concept type agnostic rules comprise applying one or more of document divisions, headers, font type, color, punctuation and spacing applied to the multiple nested child objects to generate the medical narrative view.

4. The media of claim 3, wherein the high level object and the multiple nested child objects are logically nested and are not tied to concept type.

5. The media of claim 4, wherein the concept type agnostic rules apply concatenation and punctuation to the multiple nested child objects of the high level object.

6. The media of claim 5, wherein concatenation is a space.

7. The media of claim 6, wherein a punctuation character is inserted the high level object and the multiple nested child objects.

8. The media of claim 1, further comprising:
   storing a nested grandchild object in the medical narrative view documentation template hierarchy; and
   storing the nested relationship between the nested child object and the nested grandchild object in the medical narrative view documentation template hierarchy, wherein the nested grandchild object is nested beneath the nested child object.

9. The media of claim 8, further comprising:
   leveraging concept type agnostic rules for generating a medical narrative view for the individual to provide to a care provider;
   applying the concept type agnostic rules to the nested relationship of the high level object, nested child object and nested grandchild object in the medical narrative view documentation template hierarchy to generate a medical narrative for the patient; and
   providing a graphical user interface of the medical narrative view for the patient.

10. A system useful in a computing system for nested relationship between a high level object and a child object in a medical narrative documentation template hierarchy for generating a dynamic narrative view, the system comprising:
   (a) a computer store containing objects of medical documentation for an individual, the objects of medical narrative view documentation including
   a first object of medical narrative view documentation as a high level object in the medical narrative view documentation template hierarchy,
   a second object of medical narrative view documentation as a nested child object of the high level object in the medical narrative view documentation template hierarchy,
   the nested relationship between the high level object and the nested child object in the medical narrative view documentation template hierarchy; and
   (b) a computer server, having a processor, at the healthcare information system, which computer server is coupled to the computer store and programmed to:
   leverage concept type agnostic rules for generating a medical narrative view for the patient to provide to a care provider, wherein the concept type agnostic rules include configurable concatenation or punctuation for a plurality of nested levels,
   determine and generate a graphical user interface of the medical narrative view for the patient applying the concept type agnostic rules to the nested relationship in the documentation template, wherein medical narrative view is arranged vertically and comprises narrative headings and sections for multiple of patient arrival information, patient complaints, patient history, review of patient symptoms, patient examination, patient data reviewed, patient consults, patient diagnosis and patient disposition.

11. The system of claim 10, wherein the nested child object comprises multiple nested child objects.

12. The system of claim 11, wherein the concept type agnostic rules comprise applying one or more of document divisions, headers, font type, color, punctuation and spacing applied to the multiple nested child objects and the high level object to generate the medical narrative.

13. The system of claim 12, wherein the high level object and the multiple nested child objects are logically nested and are not tied to concept type.

14. The system of claim 13, wherein the concept type agnostic rules apply concatenation and punctuation to the multiple nested child objects of the high level object.

15. The system of claim 14, wherein concatenation is a space.

16. The system of claim 15, wherein a punctuation character is inserted the high level object and the multiple nested child objects.

17. The system of claim 16, further comprising:

storing a nested grandchild object in the medical narrative view documentation template hierarchy; and storing the nested relationship between the nested child object and the nested grandchild object in the documentation template hierarchy, wherein the nested grandchild object is nested beneath the nested child object.

18. The system of claim 17, further comprising:

leveraging concept type agnostic rules for generating the medical narrative view for the individual to provide to a care provider;

applying, utilizing a processor, the concept type agnostic rules to the nested relationship of the high level object, nested child object and nested grandchild object in the documentation template hierarchy to generate the medical narrative view for the patient; and providing a graphical user interface of the medical narrative view for the patient.

* * * * *